United States Patent
Bonner et al.

(10) Patent No.: US 8,809,770 B2
(45) Date of Patent: Aug. 19, 2014

(54) DATA INDEPENDENT ACQUISITION OF PRODUCT ION SPECTRA AND REFERENCE SPECTRA LIBRARY MATCHING

(75) Inventors: Ronald F. Bonner, Newmarket (CA); Stephen A. Tate, Barrie (CA); Rudolf Aebersold, Zurich (CH); Pedro Jose Navarro Alvarez, Zurich (CH); Oliver Rinner, Zurich (CH); Lukas Reiter, Wil (CH); Ludovic Gillet, Zurich (CH)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 13/819,769

(22) PCT Filed: Sep. 14, 2011

(86) PCT No.: PCT/IB2011/002139
§ 371 (c)(1),
(2), (4) Date: Apr. 24, 2013

(87) PCT Pub. No.: WO2012/035412
PCT Pub. Date: Mar. 22, 2012

(65) Prior Publication Data
US 2013/0206979 A1    Aug. 15, 2013

Related U.S. Application Data

(60) Provisional application No. 61/383,137, filed on Sep. 15, 2010.

(30) Foreign Application Priority Data

Sep. 15, 2010    (EP) .................................... 10009595.9

(51) Int. Cl.
*B01D 59/44*    (2006.01)
*H01J 49/00*    (2006.01)

(52) U.S. Cl.
CPC ......... *H01J 49/0036* (2013.01); *H01J 49/0031* (2013.01); *H01J 49/004* (2013.01)
USPC .......................................... 250/281; 250/282

(58) Field of Classification Search
None
See application file for complete search history.

(56) References Cited

U.S. PATENT DOCUMENTS 4,818,862 A * 4/1989 Conzemius .................... 250/287
6,586,727 B2 * 7/2003 Bateman et al. ............... 250/282

(Continued)

FOREIGN PATENT DOCUMENTS

GB    2438488 A * 11/2007 .............. H01J 49/42

OTHER PUBLICATIONS

Automated Approach for Quantitative Analysis of Complex Peptide Mixtures from Tandem Mass Spectra, Venable, et al., published online Sep. 29, 2004, D0I:10.1038/NMETH705.

(Continued)

*Primary Examiner* — Andrew Smyth
(74) *Attorney, Agent, or Firm* — John R. Kasha; Kelly L. Kasha; Kasha Law LLC

(57) ABSTRACT

Systems and methods are used to store an electronic record of all product ion spectra of all detectable compounds of a sample. A plurality of product ion scans are performed on a tandem mass spectrometer one or more times in a single sample analysis across a mass range using a plurality of mass selection windows. All sample product ion spectra of all detectable compounds for each mass selection window are produced. All sample product ion spectra for each mass selection window are received from the tandem mass spectrometer using a processor. All sample product ion spectra for each mass selection window are stored as an electronic record of all detectable compounds of the sample using the processor. The electronic record is used to characterize compounds known at the time the electronic record is stored or to characterize compounds that became known after the electronic record was stored.

20 Claims, 6 Drawing Sheets

(56) References Cited

U.S. PATENT DOCUMENTS

| | | | |
|---|---|---|---|
| 6,717,130 B2* | 4/2004 | Bateman et al. | 250/282 |
| 6,940,065 B2* | 9/2005 | Graber et al. | 250/282 |
| 6,987,261 B2* | 1/2006 | Horning et al. | 250/282 |
| 7,485,853 B2* | 2/2009 | Bëβmann et al. | 250/282 |
| 7,897,405 B2* | 3/2011 | Prakash | 436/161 |
| 7,928,363 B2* | 4/2011 | Bateman | 250/283 |
| 7,972,770 B2* | 7/2011 | Tempst et al. | 435/4 |
| 8,026,479 B2* | 9/2011 | Lock et al. | 250/288 |
| 8,237,106 B2* | 8/2012 | Castro-Perez et al. | 250/281 |
| 8,269,166 B2* | 9/2012 | Okumura | 250/288 |
| 8,271,203 B2* | 9/2012 | Hunter et al. | 702/19 |
| 8,395,113 B2* | 3/2013 | Grothe, Jr. | 250/282 |
| 8,658,969 B2* | 2/2014 | Nishiguchi | 250/281 |
| 2001/0052569 A1* | 12/2001 | Bateman et al. | 250/288 |
| 2002/0063206 A1* | 5/2002 | Bateman et al. | 250/281 |
| 2002/0127609 A1* | 9/2002 | Davis et al. | 435/7.1 |
| 2003/0066802 A1* | 4/2003 | Jastorff et al. | 210/656 |
| 2004/0014143 A1* | 1/2004 | Haskins et al. | 435/7.1 |
| 2004/0108452 A1* | 6/2004 | Graber et al. | 250/281 |
| 2004/0217272 A1* | 11/2004 | Horning et al. | 250/282 |
| 2005/0221500 A1* | 10/2005 | Reid et al. | 436/86 |
| 2005/0230611 A1* | 10/2005 | Denny et al. | 250/282 |
| 2006/0289737 A1* | 12/2006 | Bassmann et al. | 250/282 |
| 2008/0021687 A1* | 1/2008 | Hunter et al. | 703/11 |
| 2009/0014639 A1* | 1/2009 | Bateman | 250/281 |
| 2009/0204337 A1* | 8/2009 | Prakash | 702/19 |
| 2009/0208921 A1* | 8/2009 | Tempst et al. | 435/4 |
| 2009/0236513 A1* | 9/2009 | Lock et al. | 250/282 |
| 2009/0302210 A1* | 12/2009 | Castro-Perez et al. | 250/282 |
| 2010/0176291 A1* | 7/2010 | Hager et al. | 250/283 |
| 2010/0311176 A1* | 12/2010 | Williamson et al. | 436/86 |
| 2011/0012017 A1* | 1/2011 | Nishiguchi | 250/282 |
| 2011/0045514 A1* | 2/2011 | Muntendam et al. | 435/15 |
| 2011/0284740 A1* | 11/2011 | Okumura | 250/288 |
| 2012/0049058 A1* | 3/2012 | Grothe, Jr. | 250/282 |
| 2013/0153761 A1 | 6/2013 | Bonner et al. | |

OTHER PUBLICATIONS

Waters Expands Xevo MS Instrument Platform With Next-Generation Mass Spectrometers, News Archive, Xevo TQ-S and Xevo G2 QTof Bring New Levels of Performance to Qualitative and Quantitative Benchtop Mass Spectrometry, Salt Lake City, Utah, May 24, 2010.

Papayannopoulos I A: "The Interpretation of Collision-Induced Dissociation Tandem Mass Spectra of Peptides," Mass Spectrometry Reviews, John Wiley and Sons, New York, NY, US, vol. 14, Jan. 1, 1995, pp. 49-73, XP001051562, ISSN: 0277-7037, DOI: 10.1002/MAS.1280140104; Scheme 1 Introduction; Section IV, and Section VI.

* cited by examiner

DATA INDEPENDENT ACQUISITION OF PRODUCT ION SPECTRA AND REFERENCE SPECTRA LIBRARY MATCHING

CROSS-REFERENCE TO RELATED APPLICATION

This application claims the benefit of U.S. Provisional Patent Application No. 61/383,137 filed Sep. 15, 2010 and European Patent Application No. 10009595.9 filed Sep. 15, 2010, which are incorporated by reference herein in their entireties.

INTRODUCTION

Mass Spectrometry has been used for many years to identify and quantitate compounds in complex mixtures. Typical compounds can include, but are not limited to, proteins, peptides, pharmaceutical compounds, and derivatives such as metabolites, drugs of abuse, pesticides, etc. A common mass spectrometry technique is tandem mass spectrometry. In tandem mass spectrometry a precursor ion is selected by a mass analyzer, fragmented in some way and the fragments analyzed in a second mass analyzer or in a second scan of the first analyzer. The fragments produced can be used for identification or quantitation.

A common technique for quantitation is selected reaction monitoring (SRM). SRM has been used for a long while to quantitate small molecules and more recently has been applied to peptides, proteins, and other biological compounds such as lipids and carbohydrates. SRM is typically performed on a triple quadrupole instrument, where the first and second mass analyzers have a mass isolation peak width of about 0.7, and one or more combinations of precursor and fragment masses (known as transitions) are monitored during a liquid chromatography coupled to mass spectrometry (LC-MS) analysis.

Despite its sensitivity and robustness, SRM has, at least, the following issues that limit its application:

1. The compounds to be measured must be defined prior to data acquisition and the transitions to be monitored must be determined, either from empirical fragment spectra of the compounds of interest or from libraries of such spectra.

2. The information obtained is incomplete since the number of transitions, and thus compounds that can be measured during a single analysis is limited for a number of reasons. The chromatographic peak must be well defined since quantitation is based on the height or area of peaks in the chromatograms of the transitions, i.e. a plot of the response for the transition vs. time. Thus it is necessary to keep the time spent measuring a set of transitions as low as possible. The sensitivity (the smallest amount of material that can be detected) depends on the length of time (the dwell time) spent monitoring a transition so better sensitivity takes more time meaning that fewer compounds can be analyzed. Confidence that the correct compound has been identified usually requires that several transitions be measured and the responses compared to those expected from the standard spectrum. This is particularly true if the mass transmission windows are relatively wide so that in complex mixtures one or more precursors or fragments could be selected at the same time and interfere with measurement of the target fragment ion(s). Precise and accurate quantitation requires inclusion of an authentic standard material, typically an isotopically labeled form of the target compound, which generates different transitions that can be distinguished from the target compound; these must also be monitored thus reducing the overall number of compounds that can be analyzed.

3. Further, the data available is limited to that defined before the analysis is performed. Therefore, it is often necessary to re-analyze the sample to generate additional data, if different or additional transitions must be monitored to improve the accuracy of confidence of the quantitation, or if additional data is required to detect different compounds or modified forms of the target compounds.

4. Since only a limited number of compounds can be analyzed at one time, obtaining data for all the compounds present in a sample requires many separate analyses.

One alternative acquisition method alternates scans with high and low fragmentation that are then processed to determine the precursors (low energy) and fragments (high energy) that belong together. Quantitation based on ion traces extracted from this data (similar to SRM) is prone to interferences since in complex mixtures many ions can be fragmented at the same time.

Other alternative acquisition methods select small mass windows that are stepped across a mass range of interest, but complete coverage of the entire mass range requires numerous analyses and takes a considerable amount of time.

Thus there is a tradeoff between the number of compounds that can be analyzed in the same analysis, and hence the sample throughput if complete coverage is required, the sensitivity, and the likelihood of detecting interferences that degrade the quantitation behavior.

BRIEF DESCRIPTION OF THE DRAWINGS

The skilled artisan will understand that the drawings, described below, are for illustration purposes only. The drawings are not intended to limit the scope of the present teachings in any way.

Figure 1:
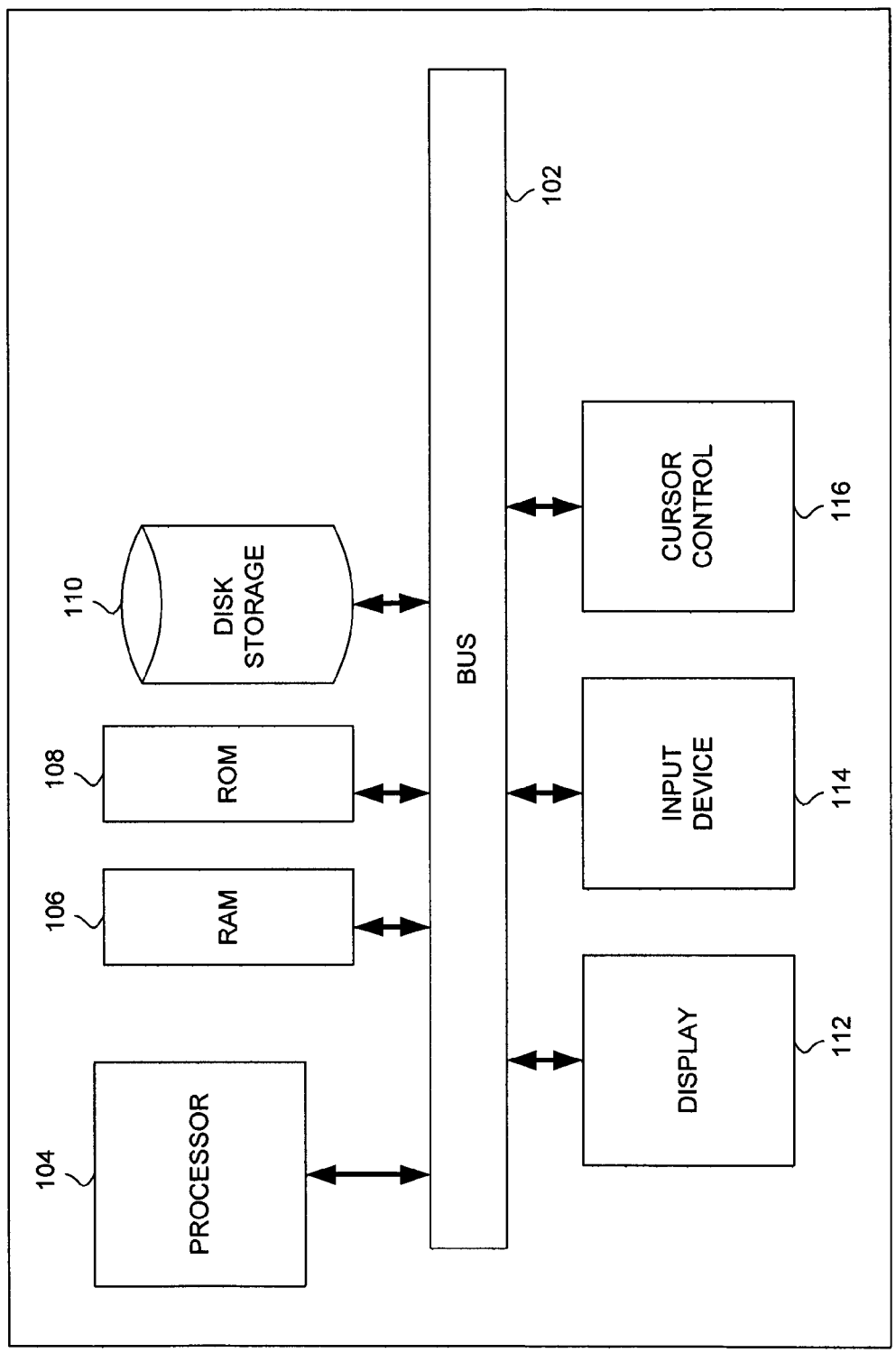
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods of Data Processing

As described above, in traditional mass spectrometry methods there is a tradeoff between the number of compounds that can be analyzed in the same analysis and the sensitivity and the likelihood of detecting interferences that degrade the quantitation behavior.

Thus there is a need for a method that provides a complete record of all detectable compounds present in a complex mixture that can be used to quantitate known compounds, determine and quantitate modified forms of the known compounds, or to determine the type and location of unknown modification. Further, the record should be stored so that these operations can be performed at the time that data is acquired or at some later time. Such a record enables the complete analysis of all compounds that can be detected with the separation device and mass spectrometer system used.

This method allows dynamic quantitative target transitions and modified forms of the target compounds (such as metabolites or post-translational modifications) to be determined without re-acquiring data on the sample.

In various embodiments, systems and methods provide a method for generating a record of all detectable compounds and comprise a novel combination of a data acquisition method that generates the fragment spectra of all compounds and targeted data analysis methods.

Current selected reaction monitoring (SRM) methodology requires lengthy preparatory work to devise the method prior to the sample injection (including the reference spectra library generation); it allows monitoring transitions of a limited number of peptides per injection; it requires extensive data analysis by reference library matching to confirm the identity of the peptides monitored; and it requires new data acquisition to improve quantification accuracy (by replacing contaminated transitions by new ones) and/or to expand the quantification to new transitions and/or analytes not monitored in the original data set.

In various embodiments, systems and methods address the current limitations of the SRM approach and enable the probing of entire proteomes iteratively and recursively from a single sample injection. Although these systems and methods address the current limitations of the SRM approach, they are not limited in any way to SRM or the type of experiments for which SRM is applied. These systems and methods comprise a combination of a novel LC-MS acquisition set-up together with a bioinformatic pipeline for the data analysis. Details of various embodiments are presented below:

Method Set-Up

Contrary to SRM, various embodiments do not require any preliminary method design prior to the sample injection. Since the LC-MS acquisition can cover the complete analyte content of a sample across the recorded mass and retention time ranges (see below), the data can be mined a posteriori for any compound of interest. The retention time and mass ranges may be set to generate information for ranges of particular interest.

LC-MS Acquisition Method

In various embodiments an acquisition method covers all compounds detectable with the chromatography and mass range used; these can be broad and generic to detect as many compounds as possible or can be adjusted to focus on compounds or types of compounds of particular interest. A wide window of precursor ions, for example >10, >15, >20 amu, is selected and fragmented to generate a fragment spectrum of all precursor present in the window. The window is moved in a step wise manner to cover the rest of the precursor space, for example, with a window width of 25 amu the first window may cover 100-125, the second 125-150, the third 150-175, and so on.

The windows can be overlapped to make sure that all the isotopic forms of a compound are present together in at least one window. It is beneficial for the windows to have relatively square shapes so that overlap can be kept small and minimize the number of windows required.

Thus the time required to acquire data for the entire mass range depends on the number of and accumulation time of windows and not the number of precursors to be fragmented. The time is short enough to maintain the fidelity of peaks produced by the separation.

Generating product ion spectra for the entire mass range is repeated one or more times depending on whether a separation system is used. A mass spectrum of all unfragmented precursor ions can be included as part of the cycle. All of the acquired data is stored for later mining. The width of the windows can be constant or can be varied.

Figure 2:
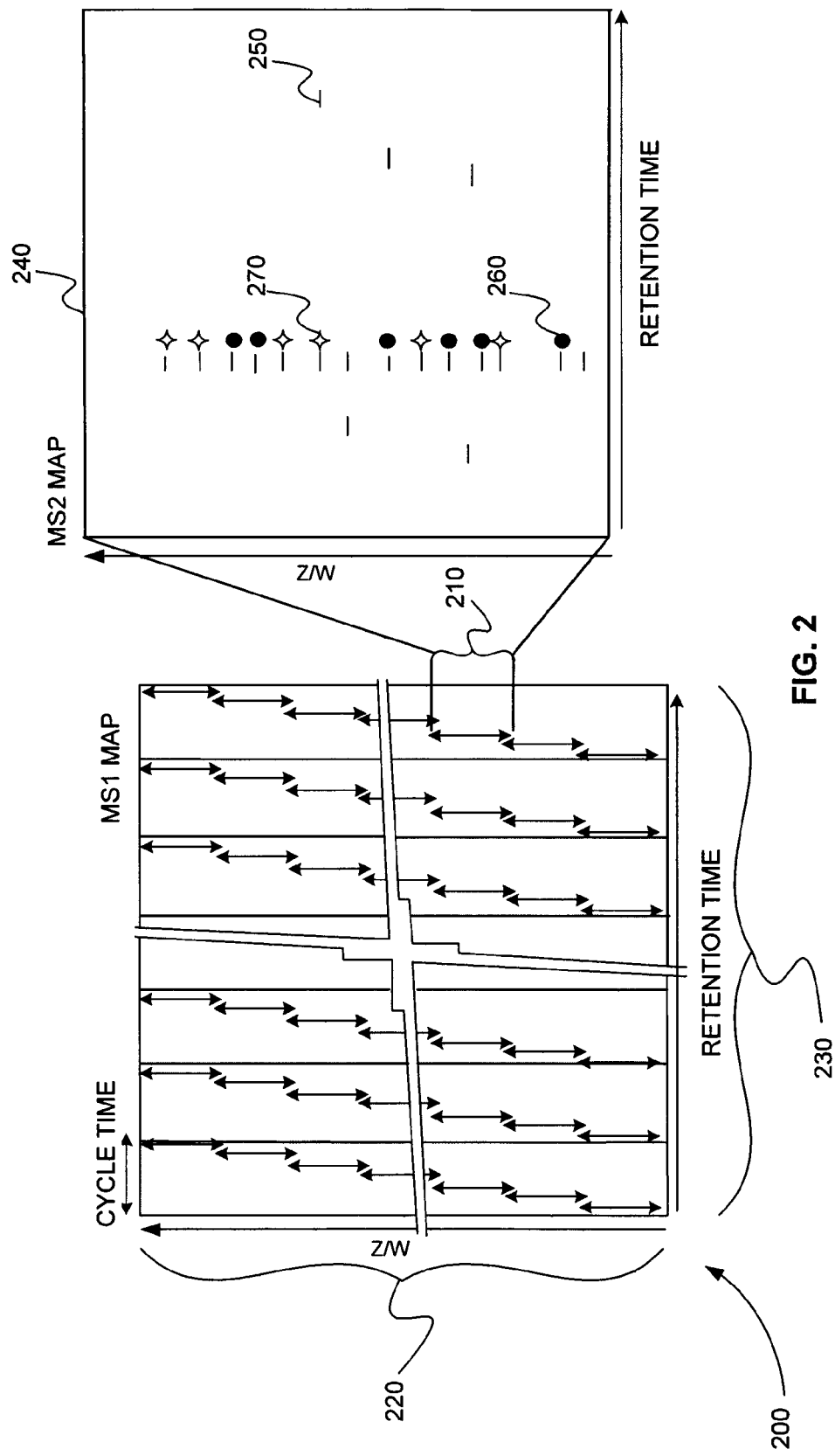
FIG. 2 is a schematic diagram showing how data is acquired for a complete mass range using step-wise precursor ion selection windows of a mass analyzer, in accordance with various embodiments.

FIG. 2 is a schematic diagram 200 showing how data is acquired for a complete mass range using step-wise precursor ion selection windows of a mass analyzer, in accordance with various embodiments. Diagram 200 depicts an LC-MS method in which a data independent acquisition of full fragment ion spectra is obtained by panning isolation windows of a mass analyzer, step by step, across the entire mass range 220 repeatedly during an entire chromatography 230. Diagram 200 is an LC-MS map, for example. Note that the dotted line before the beginning of each cycle in diagram 200 depicts the optional acquisition of a high-resolution, accurate mass survey (MS1) scan that can also be used to re-associate the fragment ions to the precursor they originate from, if needed for the analysis processes.

The data of diagram 200 can be interpreted by combining the product ion spectra acquired for each isolation window into separate MS2 maps. MS2 map 240 is an exemplary combination of all the product ion spectra for isolation window 210. MS2 map 240 includes ion traces 250 plotted as a function of mass over charge (m/z), retention time and signal intensity. Symbol 260 identifies ion traces 250 of fragments belonging to corresponding analytes. Symbol 270 identifies ion traces 250 of fragments determined from a reference spectra library.

Figure 3:
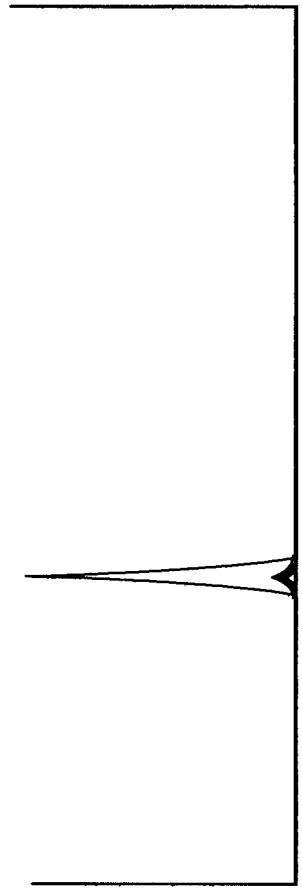
FIG. 3 is an exemplary plot showing the mass traces extracted from the ion traces of FIG. 2 for fragments determined from a reference spectra library, in accordance with various embodiments.

FIG. 3 is an exemplary plot 300 showing the mass traces extracted from the ion traces of FIG. 2 for fragments determined from a reference spectra library, in accordance with various embodiments.

In various embodiments, an LC-MS acquisition method comprises the monitoring of product ions resulting from the fragmentation of ion precursors as follows:

Complete Content Coverage for all the Analytes of a Sample:

1) Data independent acquisition upon stepping of the isolation window of the mass analyzer:

Instead of monitoring a few discrete precursors/transitions per run, MS information is acquired in a data independent manner, on the full mass range and through the entire chromatography, irrespective of the content of the sample. In various embodiments, this can be achieved by stepping the precursor ion selection window of the mass analyzer step by step through the complete mass range (see FIG. 2), instead of focusing on pre-determined or targeted precursors. The cycle time (or dwell time) of these measurements is thus determined by the number of steps necessary to cover the complete mass range (FIG. 2) rather than by the number of transitions to be monitored as in SRM. Such step-wise, data-independent fragmentation measurements allow the acquisition of the complete information on the analytes/precursors contained in a sample in one single run. In effect, this data acquisition method can generate a complete fragment ion map for all the analytes present in the sample and relate the fragment ion spectra back to the precursor ion selection window in which the fragment ion spectra were acquired.

2) Widening of the selection window of the first mass analyzer:

2a) It is almost impossible, even at the narrowest selection window achievable by the mass analyzer, to ensure that only the precursor of interest, free of contaminants, is selected for fragmentation. Therefore, in various embodiments, an opposite approach is used: widening the precursor isolation windows of the mass analyzer and thus including multiple precursors co-eluting and contributing to the fragmentation pattern recorded during the analysis. The interpretation of complex product ion spectra resulting from multiple precursors' fragmentation is described below in the data analysis section.

2b) Collateral positive effects of widening the selection window of the mass analyzer as practiced in various embodiments, are (i) the shortening of the cycle time mentioned in point (1) and thus the acquisition of better defined and resolved chromatographic elution profiles for the precursors monitored; and (ii) an increased signal intensity for the fragments since the entire isotopic pattern of the precursor now participates in the fragmentation, and not only the mono-isotopic peak as in SRM.

Gain in Confidence for the Peptide Identifications:

3) Acquisition of full product ion spectra, instead of monitoring a few product ions for a given precursor as in classical SRM experiments. A series of full product ion (MS2) spectra is acquired across the elution of a precursor allowing better confidence in the precursor identification to be achieved by matching the complete fragmentation pattern of a full MS2 spectra to a reference spectrum from a library, rather than a few ion fragments.

In summary, in various embodiments an LC-MS method results in the acquisition of a series of MS2 maps that can cover the complete mass range and chromatographic profile and that can be processed as pseudo-SRM traces acquired on wide isolation windows (FIGS. 2-3) instead of few transitions per precursor.

Consecutive MS2 maps may be acquired with some precursor isolation window overlap to ensure transfer of the complete isotopic pattern of any given precursor ion in at least one isolation window and thereby to maintain optimal correlation between parent and fragment isotopes peaks at any LC time point. This overlap may be reduced to a minimum value, which can be experimentally determined to best match the fragment ion transmission profile achievable on the ion selection devices used in the mass spectrometer. Reducing the overlap between consecutive isolation windows allows to maintain a minimal size for the windows, a minimal number of windows to cover a given m/z range and a minimal dwell time between the cyclic isolation window acquisitions.

Various embodiments include the following MS acquisition methods in various combinations; and alone and together with various combinations of the data analyses principles described further below:

1) The cyclic acquisition of full fragmentation (MS2) spectra of precursor ions upon stepping the precursor isolation window of the mass analyzer in a content-independent manner (see FIG. 2). The acquisition does not include, e.g., focusing the precursor isolation windows onto the masses of predetermined (e.g., data dependent acquisition/shotgun) or targeted (e.g., inclusion lists or SRM) precursor ions.

2) The deliberate search of these MS2 spectra for multiple parent precursors concomitantly selected within the parent ion precursor isolation windows and concomitantly participating in the observed fragmentation pattern, by various embodiments of the inventions described in the data analysis section. In other words, in various embodiments a search is not conducted for the precursor ions. A search is conducted for the fragments in the window that is expected to contain the precursor ion.

3) The use of overlapping windows for the precursor selection. Overlapping windows can be used in various embodiments to insure (i) that all the precursor ions are properly selected, even in the case of non-ideal mass analyzers and (ii) that the percursor ions at the border of the mass analyzer/ selection windows get their whole or substantially whole isotopic pattern selected for fragmentation within a same isolation window.

4) The use of fixed and/or variable widths for the precursor isolation windows during the same acquisition run. In various embodiments, fixed and/or variable widths are used for the precursor isolation windows during the same cycle (i.e., set of scans across the mass range. The use of larger windows allows for the shortening of the cycle time of the acquisition in the less crowded parts of the mass/chromatographic space (i.e., where the least number of analytes are expected). The use of a narrower window can allow for an increased dynamic range of analysis in the most complex parts of the mass/ chromatographic space. Indeed, narrower windows contain fewer precursor ions to fragment and therefore have lower chance to include precursors with large differences in abundances.

5) The use of single and/or multiple (variable or discrete) collision energies per precursor selection windows during the same acquisition run. The increasing or decreasing fragment ion intensities acquired during such multiple collision energy experiments can be checked for co-elution and correlated to reference fragment ion intensities from spectra libraries and can strengthen the identification of fragment ion peak groups that originate from the same parent ion (see the data analysis section).

6) The use of fixed and/or variable time per precursor isolation windows for the acquisition of the MS2 spectra during the same acquisition run. Since the signals can be reported as counts over acquisition time (e.g., cts/msec), the variable acquisition time can still be used for quantification purposes (as in "dynamic" or "scheduled" SRM). Longer acquisition times can allow the monitoring of low abundant precursors with more sensitivity.

Various Embodiments Concerning the Bioinformatics/Data Analysis Pipeline

The data analysis comprises the use of fragment ion elution information and data mining of reference spectra libraries. Reference spectra libraries of proteotypic peptides (MS-observable peptides uniquely found in one protein and therefore qualitatively and quantitatively unambiguously characterizing that protein) may be generated for entire organisms using pools of synthetic peptides (Picotti et al, Nat Methods 2010) and/or from prior extensive MS sequencing proteomic analyses performed on those organisms. Similarly, the reference spectra libraries of other analytes may be generated from synthetic analyte references and/or from prior analytes MS analyses. Importantly, once the reference fragment ion libraries have been generated they can be used perpetually.

Since the LC-MS data comprises full product ion spectra acquired from wide precursor selection windows, the data processing is modified to account for multiple precursors potentially participating in the fragmentation patterns observed in the recorded MS2 spectra and for the presence of all fragment ions.

Searching for Precursors a Posteriori

Contrary to the SRM approach, where the precursors of interest have to be selected prior to the sample injection, a "complete content coverage" acquisition approach enables one to search and quantify, a posteriori in the LC-MS/MS dataset, and in various embodiments any analyte present in the spectra library. The data analysis comprises the extraction of the fragment mass traces (determined from the reference spectra library and/or from in silico predictions) of the precursor of interest from a series of full product ion spectra acquired in the expected selection window (m/z) of that precursor (see FIGS. 2-3).

The confidence in the precursor identification can be scored, for example, based on the mass accuracy and/or the relative intensities of the acquired product ion fragments compared to that of the reference (or predicted) fragmentation spectrum, on the number of matched fragments, on the similar chromatographic characteristics (co-elution, peak shape, etc.) of the extracted ion traces of these fragments. Probabilities for the identifications can be determined, for example, by searching (and scoring) similarly for decoy precursor fragment ions from the same LC-MS dataset. The relative quantification can be performed by integration of the product ions traces across the chromatographic elution of the precursor. In various embodiments, use is made of differently isotopically labeled reference analytes (similarly identified, quantified and scored) to achieve absolute quantification of the corresponding precursors of interest.

Gain in Confidence for the Peptide Identifications:

A series of full product ion (MS2) spectra can be extracted around the elution of the best scoring fragment ion peak group candidates to achieve better confidence in the precursor identification by matching the complete fragmentation pattern of a full MS2 spectrum to a reference spectrum from a library, rather than a few ion fragments.

The data mining strategy described above uses an unbiased extraction, from the LC-MS/MS dataset, of reference fragment ion traces (from spectra libraries). The full product ion maps are, therefore, mined for the identification of multiple precursors, since those are extracted with fragment ion traces of independent matches from the library. Therefore this does not restrict the search number of precursors co-eluting within the selection window of the mass analyzer and can allow for the identification of multiple precursors within the same product ion spectra.

Alternative Data Processing by MS2 Feature Extraction

Another data processing embodiment comprises a de novo feature extraction of all or substantially all of the fragment ion signals from the reconstituted MS2 maps (FIG. 2). The co-eluting fragment ion signals can then be grouped and searched by reference spectra library matching (or eventually against a database of pre-computed theoretical fragment ions of analytes) to determine their precursor(s) of origin. In various embodiments, the method proceeds by iteration of precursor identification and subtraction of the product ion signals of that precursor across its elution to increase the sensitivity of the analysis and uncover ion fragments of precursors of lower abundances.

Various embodiments include the following data analysis principles in various combinations; and alone and together with various combinations of the MS acquisitions principles described further above:

1) The extraction of the fragment mass traces (determined from the reference spectra library or from in silico predictions) of the precursor of interest from the series of full product ion spectra acquired in the expected selection window (or windows, for modified or multiple charge states peptides) of that precursor (see FIGS. 2-3)

2) The identification of the analytes by scoring the extracted fragment ion traces based on parameters such as, for example: (i) co-elution of the extracted fragment ion traces, (ii) correlation of their peak shapes, (iii) correlation of their relative intensities with those from a reference spectra library (or from in silico predictions), (iv) proximity to the expected reference chromatographic retention time, (v) co-elution and peak shape correlation of the fragment ion traces of multiple charge states of the same precursor, (vi) co-elution, peak shape and relative intensity correlation with the fragment ion traces of one or more differently isotopically labeled reference(s) (e.g., heavy or light reference analyte for a light or an heavy endogenous sample respectively), (vii) co-elution and peak shape correlation of the fragment ion traces obtained from the windows acquired at various collision energies, (viii) correlation of the relative intensities of the fragments ions obtained from the windows acquired at various collision energies with those a reference spectra library (or from in silico predictions), and (ix) combinations of two or more of the above.

3) The discrimination of true from false positives identifications by false discovery rate evaluation upon searching (and scoring) similarly the same LC-MS/MS dataset for decoy precursor fragment ions. The decoy hits can substantially be used to optimize the combination of one or more of the scores mentioned above using machine learning techniques (e.g., semi-supervised learning) and to estimate a false discovery rate by assuming that they resemble the null distribution of identifications.

4) The use of the co-eluting fragment ion intensities to quantify the identified analytes contained in the sample.

5) The "refinement" and the re-searching (e.g., in multiple iterations) of the acquired data by substantially removing, across their chromatographic elution, the contaminated fragment ion traces or those of already identified analytes.

6) The extraction of pre-computed theoretical fragment mass traces of any precursor of interest from the series of full product ion spectra acquired in the expected selection window (or windows, for modified or multiple charge states peptides) of that precursor (e.g., for the acquisition and refinement of spectra libraries of natural or synthetic compounds)

7) The de novo "feature extraction" of the fragment ion signals from the reconstituted MS2 maps (FIG. 2); the grouping and scoring of those fragment ion signals as, e.g., described above (point 2); the searching of those by reference spectra library matching (or eventually against a database of pre-computed theoretical fragment ions of analytes) to determine their precursor(s) of origin; the quantification of the identified analytes based on their co-eluting fragment ion intensities.

In summary, various embodiments can allow for (i) the exhaustive acquisition of the product ion spectra of all analytes present in a sample, in a single LC-MS injection or analysis, (ii) the complete identification and quantitative analysis of those by a specific data mining strategy, and (iii) the refinement and/or complementation of those analyses by iterative data mining. This combined LC-MS acquisition and data processing methodology constitutes therefore a significant improvement over the traditional approach in terms of data consistency, identification rates and quantification speed. These inventions enable the acquisition of complete proteome maps and the methods for the qualitative and quantitative data mining of those.

The potential applications of these inventions are essentially the same as those of SRM quantitative proteomics and include any biotechnical, biomedical, pharmaceutical and biological applications that rely on qualitative and quantitative LC-MS analysis. The approaches are, for example, in various embodiments particularly suited to perform the analysis of a high number of candidate precursors (e.g., peptides) of interest in complex samples that may be available only in limited amounts (e.g., complete organisms, cells, organs, bodily fluids, etc.).

Various embodiments include the following applications, among others:

Rapid acquisition and refinement of spectra libraries of natural or synthetic compounds (e.g., peptides).

Qualitative and quantitative analysis of natural or synthetic compounds of interest (e.g., in the context of specific analytes or biomarkers measurements, or to analyze the composition of protein complexes).

Qualitative and quantitative analysis of naturally or artificially modified analytes that share fragment ions with their non-modified counter-parts (e.g., proteins/peptides with post-translational modifications, reacted with activity-based probes, or chemically cross-linked proteins/peptides), or whose modification share fragment ions (e.g., ubiquitin or ubiquitin-like molecules) or common reporter ions or by using the (positive or negative) mass difference that this modification brings to the fragment ions of those analytes.

Qualitative and quantitative analysis of all detectable analytes present in spectra libraries or de novo identified (see data analysis section) (e.g., in the context of partial or complete proteome analyses).

The capacity to refine and/or complement of those qualitative and quantitative analyses by iterative data mining of the acquired datasets.

These various embodiments can pave the way for the complete qualitative and quantitative analysis of entire metabolome/proteome of complex samples and in a high throughput manner.

Quantitative Data Processing

In various embodiments, all of the fragment data acquired from a single precursor mass window can be processed together. Even though the data may contain fragments from one or more precursor ions (compounds), it can be processed to quantitate the compound of interest or search for modified forms of such compounds.

The precursor mass of the compound of interest and a set of expected fragments at high resolution and mass accuracy are obtained from a library, or by analyzing an authentic standard form of the compound, or obtained from a previous analysis (whether the compounds are known or not), or by prediction using known fragmentation rules. The set of fragments can be selected based on their expected intensity, the likelihood that that they are unique to the compound of interest, or other features. For the window(s) containing the expected precursor mass, the set of fragment masses are used to generate ion traces, for example chromatograms, that include one or more peaks The traces are scored to determine the correct or most likely peak. The score can be based on information from the mass spectrum such as: how well the detected mass of the sample fragment ions match the expected masses of the predetermined product ions; how well the relative intensities of the sample fragment ions match the relative intensities of the predetermined product ions; that the measured sample ions are in the correct isotopic form, usually that they are monoisotopic; that the precursor and fragment ions have the expected charge state.

If a separation step is included, the score can be based on additional information such as: how well the detected ion traces match each other in shape and position. If different isotopic forms of the sample are analyzed, such as a combination of labeled and native forms, data from the different forms can be used to further refine the score. If one or more fragments in the set receive poor scores because there is an interference, they can be excluded from the set and, if desired, replaced with another fragment from the predetermined spectrum.

Ions that receive acceptable scores can be used to generate quantitative values for the target compound that can be compared to similar values from other samples, such as members of a time course study, groups of samples that have been treated or prepared differently, groups of samples from healthy or diseased subjects, etc. As all fragment ions from all detected precursor exist in the data, in various embodiments optimal quantitation can be performed by using alternative fragment ions which reduce error in measurement.

Since the acquired data includes fragments from all detectable compounds, it can be mined for any number of compounds and the scoring can generate quantitative values.

Qualitative Data Processing

In various embodiments, the data can be further mined to extract qualitative information about the compounds present in the sample. Modified forms can be detected by locating the same set of fragment ions at unexpected retention times in the same precursor window or in different windows, for example.

The window can be determined based on the expected mass difference caused by the modification. In various embodiments, modified forms can be detected by locating ions that are characteristic of the modification.

Once a modified form is detected the type and location of the modification can be determined in a number of ways. For example, the type and location of the modification can be determined by predicting ions that depend on the position or type of the modification and generating and scoring traces extracted from the data for those predicted masses. In various embodiments, the type and location of the modification can be determined by generating a spectrum from the data and interpreting that spectrum.

Further, the data from each window can be processed to determine or identify related ions and thereby extract the spectrum of known or unknown compounds that can be interpreted to determine the identity of the compound.

Tandem Mass Spectrometry System

Figure 4:
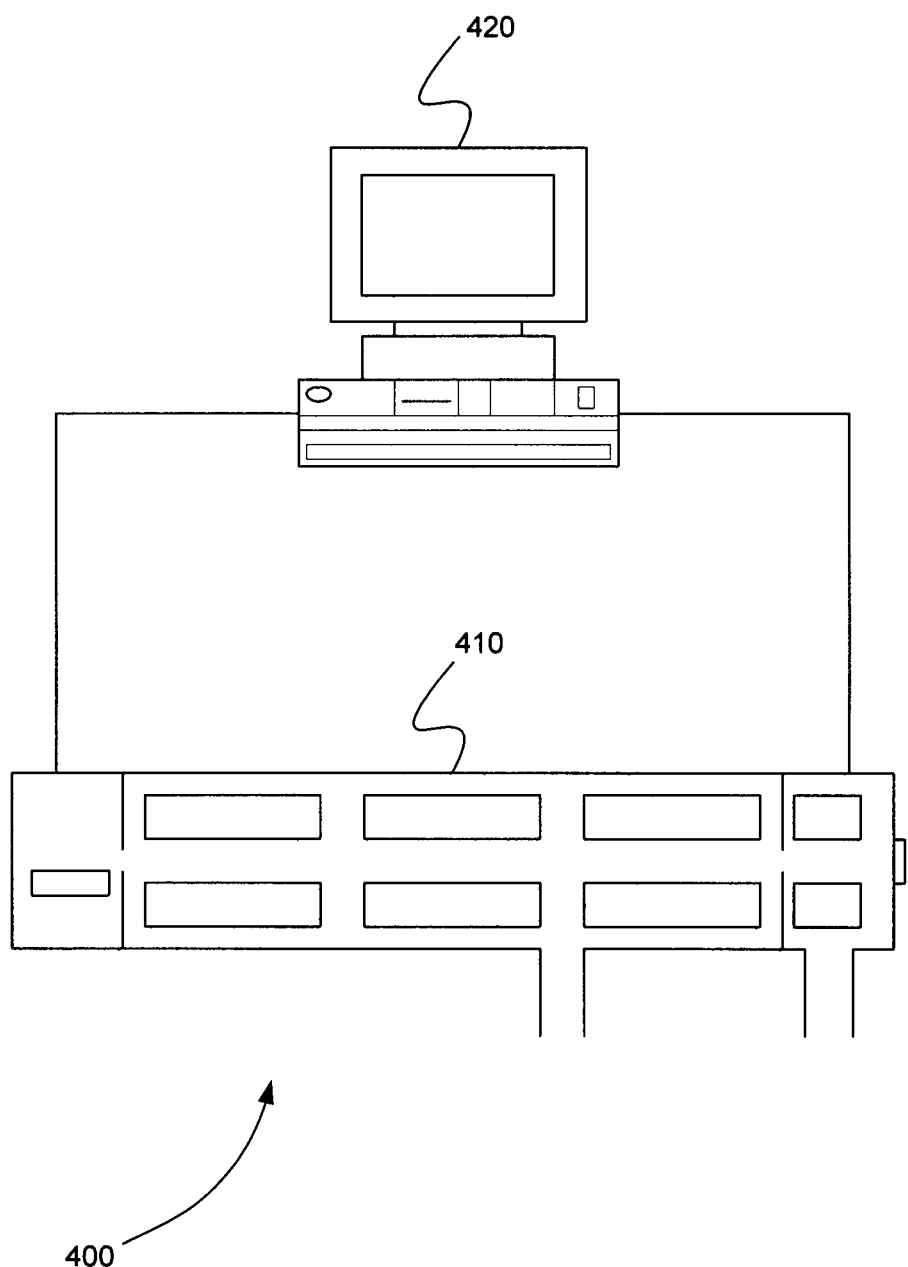
FIG. 4 is a schematic diagram showing a system for storing an electronic record of all product ion spectra of all detectable compounds of a sample, in accordance with various embodiments.

FIG. 4 is a schematic diagram showing a system 400 for storing an electronic record of all product ion spectra of all detectable compounds of a sample, in accordance with various embodiments. System 400 includes tandem mass spectrometer 410 and processor 420. Processor 420 can be, but is not limited to, a computer, microprocessor, or any device capable of sending and receiving control signals and data from mass spectrometer 410 and processing data.

Tandem mass spectrometer 410 can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, or a Fourier transform mass analyzer. Tandem mass spectrometer 410 can also include a separation device (not shown). The separation device can perform a separation technique that includes, but is not limited to, liquid chromatography, gas chromatography, capillary electrophoresis, or ion mobility. Tandem mass spectrometer 410 can include separating mass spectrometry stages or steps in space or time, respectively.

Tandem mass spectrometer 410 performs a plurality of product ion scans one or more times across a mass range using a plurality of mass selection windows. The plurality of product ion scans are performed in a single sample analysis. A single sample analysis is, for example, a single sample injection. From the plurality of product ion scans, tandem mass spectrometer 410 produces all sample product ion spectra of all detectable compounds for each mass selection window.

Processor 420 is in communication with tandem mass spectrometer 410. Processor 420 receives all the sample product ion spectra for each mass selection window from tandem mass spectrometer 410. Processor 420 then stores all sample product ion spectra for each mass selection window as an electronic record of all detectable compounds of the sample. The electronic record is used to characterize compounds known at the time the electronic record is stored or to characterize compounds that became known after the electronic record was stored.

In various embodiments, each mass selection window of the plurality of mass selection windows has a width greater than 10 atomic mass units (amu), or a width greater than 15 amu.

In various embodiments, at least two mass selection windows of the plurality of mass selection windows have different widths.

In various embodiments, all sample product ion spectra for one or more mass selection windows from the electronic record are searched for predetermined product ion spectra from a reference library. For example, processor 420 receives predetermined product ion spectra corresponding to known compounds. Processor 420 receives all sample product ion spectra for one or more mass selection windows from the electronic record. Processor 420 then compares predetermined product ions of the predetermined product ion spectra to sample product ions of said all sample product ion spectra for one or more mass selection windows. One or more matching sample product ions from the comparison characterize the known compounds detectable in the sample. The known compounds include, for example, any compound that gives reproducible product ion spectra.

In various embodiments, the known compounds include one or more of peptides, proteins, complete proteomes, endogenous metabolites, lipids, or carbohydrates.

In various embodiments, the known compounds include one or more compounds of biological, pharmaceutical, environmental, forensic, or industrial importance. The one or more compounds of biological, pharmaceutical, environmental, forensic, or industrial importance can include, but are not limited to, one or more of pesticides, herbicides, fungicides, industrial chemicals, drugs of abuse, dopants or explosives.

In various embodiments, the predetermined product ion spectra are computationally generated by applying empirical or a priori fragmentation or modification rules to the known compounds.

In various embodiments, the predetermined product ion spectra are obtained from the analysis of authentic standard compounds, either isolated from a naturally occurring source or chemically synthesized.

In various embodiments, the predetermined product ion spectra are obtained from public or proprietary spectral libraries.

In various embodiments, the predetermined product ion spectra are obtained from a prior analysis of a representative sample with or without identification of compounds corresponding to the predetermined product ion spectra.

In various embodiments, the search for predetermined product ion spectra from a reference library includes calculating a score. For example, processor 420 compares predetermined product ions of the predetermined product ion spectra to sample product ions of all sample product ion spectra for one or more mass selection windows by calculating a score that represents how well the predetermined product ions and the sample product ions match. The score can, for example, can include comparing ion masses and relative intensities. In various embodiments, the score includes determining that the sample precursor ion has the expected isotopic form. In various embodiments, the score can include information on the expected charge state of the precursor and fragment ions.

In various embodiments, a separation device separates sample compounds of the single sample analysis over time. Tandem mass spectrometer 410 performs a plurality of product ion scans on the single sample analysis as the sample compounds are being separated. In various embodiments, processor 420 further calculates a score for the match based on comparing peak shapes of ion traces or detection time similarity of matching sample product ions.

In various embodiments, processor 420 further uses one or more matching sample product ions from the comparison of the search to calculate a quantitative value for compounds of the sample. The quantitative value is, for example, calculated using an intensity of the one or more matching sample product ions in the sample product ion spectra. In various embodiments, the quantitative value is calculated using an intensity or areas of one or more matching ion trace peaks.

In various embodiments, processor 420 further uses one or more matching sample product ions from the comparison of the search to identify a modified form of one or more compounds of the known compounds. A modified form is identified by finding the one or more matching sample product ions in the same mass selection window or in different mass selection windows, for example. A different mass selection window is determined from the mass of an expected modification, for example.

In various embodiments, the modified form is identified by finding a mass corresponding to the one or more matching sample product ions adjusted by the mass of a modification. The modification is a known modification, is caused by known reactions, or is suggested by other experiments, for example.

In various embodiments, the modified form is identified by finding a mass characteristic of modified parts of the known compounds.

In various embodiments, the modified form is identified by finding complex composite spectra from conjoined molecules.

In various embodiments, processor 420 further extracts a spectrum of an identified modified form from the electronic record in order to characterize a type and location of the modification in the identified modified form.

In various forms, processor 420 further uses the predetermined product ions and the modification to predict masses that would indicate the site of the modification and generates a score for each said mass to determine the location of the modification.

Tandem Mass Spectrometry Method

Figure 5:
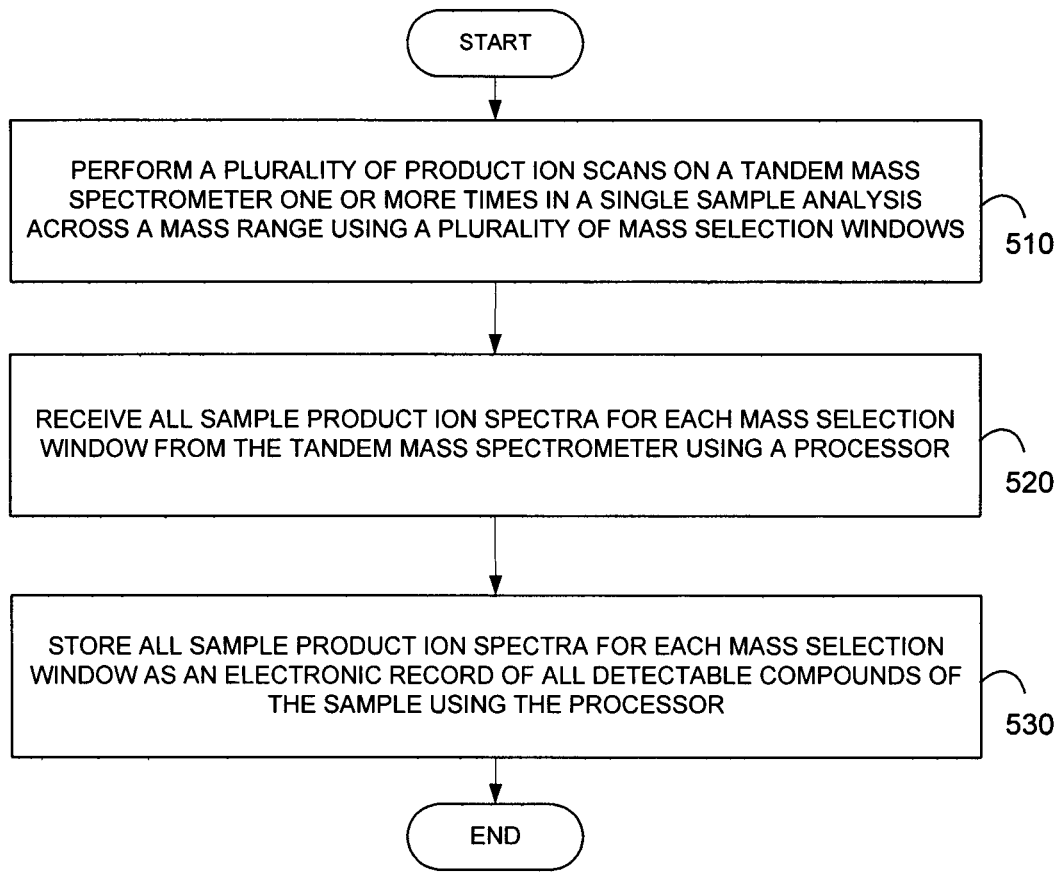
FIG. 5 is an exemplary flowchart showing a method for storing an electronic record of all product ion spectra of all detectable compounds of a sample, in accordance with various embodiments.

FIG. 5 is an exemplary flowchart showing a method 500 for storing an electronic record of all product ion spectra of all detectable compounds of a sample, in accordance with various embodiments.

In step 510 of method 500, a plurality of product ion scans are performed on a tandem mass spectrometer one or more times in a single sample analysis across a mass range using a plurality of mass selection windows. All sample product ion spectra of all detectable compounds for each mass selection window are produced.

In step 520, all sample product ion spectra for each mass selection window are received from the tandem mass spectrometer using a processor.

In step 530, all sample product ion spectra for each mass selection window are stored as an electronic record of all detectable compounds of the sample using the processor. The electronic record is used to characterize compounds known at the time the electronic record is stored or to characterize compounds that became known after the electronic record was stored.

Tandem Mass Spectrometry Computer Program Product

In various embodiments, a computer program product includes a tangible computer-readable storage medium whose contents include a program with instructions being executed on a processor so as to perform a method for storing an electronic record of all product ion spectra of all detectable compounds of a sample. This method is performed by a system that includes one or more distinct software modules.

Figure 6:
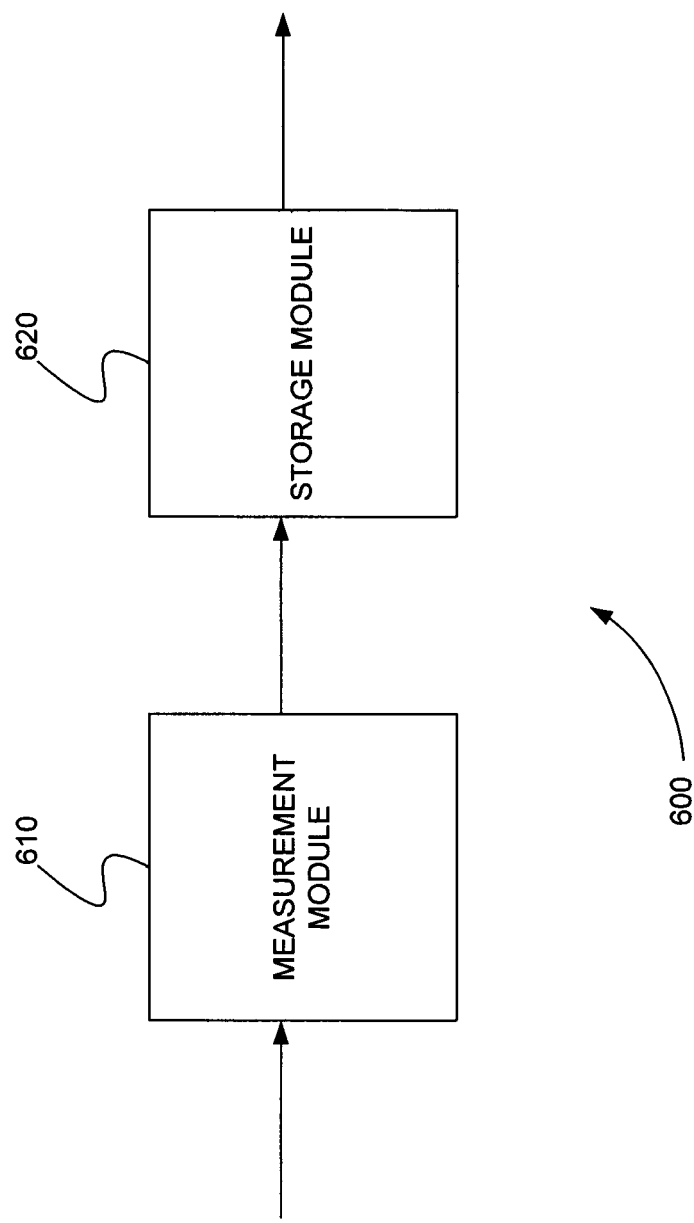
FIG. 6 is a schematic diagram of a system that includes one or more distinct software modules that performs a method for storing an electronic record of all product ion spectra of all detectable compounds of a sample, in accordance with various embodiments.

FIG. 6 is a schematic diagram of a system 600 that includes one or more distinct software modules that performs a method for storing an electronic record of all product ion spectra of all detectable compounds of a sample, in accordance with various embodiments. System 600 includes a measurement module 610 and a storage module 620.

Measurement module 610 receives from a tandem mass spectrometer all sample product ion spectra of all detectable compounds for each mass selection window of a mass range.

The tandem mass spectrometer produces the sample product ion spectra by performing a plurality of product ion scans one or more times in a single sample analysis across the mass range using a plurality of mass selection windows.

Storage module 620 stores all sample product ion spectra for each mass selection window as an electronic record of all detectable compounds of the sample. The electronic record is used to characterize compounds known at the time the electronic record is stored or to characterize compounds that became known after the electronic record was stored.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for quantitating detectable compounds of a sample, comprising:
   a processor that receives sample product ion spectra for each mass selection window of a plurality of precursor mass selection windows for each time step of a plurality of time steps,
   wherein the sample product ion spectra are produced by separating detectable compounds in a sample over time, and at each time step analyzing the detectable compounds by performing a plurality of product ion scans for a plurality of precursor mass selection windows selected across a mass range of the sample using a tandem mass spectrometer; and
   searches the received product ion spectra for the presence of one or more known compounds with known product ion spectra by:
   a) retrieving the known product ion spectra from a library,
   b) retrieving the sample product ion spectra corresponding to the precursor mass selection window expected to contain a precursor ion corresponding to the known product ion spectra,
   c) generating product ion traces in time for the sample product ion spectra for one or more of the known product ion spectra,
   d) calculating a score for the product ion traces and product ion spectra that represents how well the known product ions and sample product ions match, and
   e) calculating a quantitative value for a known compound from the product ion traces when the score exceeds a threshold value.

2. The system of claim 1, wherein each mass selection window of the plurality of mass selection windows has a width greater than 15 amu.

3. The system of claim 1, wherein the known compounds comprise one or more of peptides, proteins, complete proteomes, endogenous metabolites, lipids, carbohydrates, or combinations thereof.

4. The system of claim 1, wherein the known compounds comprise one or more compounds of pharmaceutical, environmental, forensic, or industrial importance.

5. The system of claim 1, wherein the known product ion spectra are determined from authentic standards of the known compounds, from an analysis of samples containing the compounds, from existing spectral libraries, or computationally generated by applying empirical or a priori fragmentation or modification rules to the known compounds.

6. The system of claim 1, wherein the processor further uses one or more matching sample product ions from step d) to identify a modified form of one or more compounds of the known compounds.

7. The system of claim 6 wherein the processor compares the matching sample ions to masses predicted from known product ions and the modification to characterize a type and location of the modification.

8. The system of claim 6, wherein the processor further extracts a spectrum of the identified modified form from the sample product ion spectra in order to characterize a type and location of the modification in the identified modified form.

9. A method for quantitating detectable compounds of a sample, comprising:
   receiving sample product ion spectra for each mass selection window of a plurality of precursor mass selection windows for each time step of a plurality of time steps using a processor, wherein the sample product ion spectra are produced by separating detectable compounds in a sample over time, and at each time step analyzing the detectable compounds by performing a plurality of product ion scans for a plurality of precursor mass selection windows selected across a mass range of the sample using a tandem mass spectrometer; and
   searching the received sample product ion spectra for the presence of one or more known compounds of interest with known product ion spectra using the processor by:
   a) retrieving the known product ion spectra from a library,
   b) retrieving the sample product ion spectra corresponding to the precursor mass selection window expected to contain a precursor ion corresponding to the known product ion spectra,
   c) generating product ion traces in time for the sample product ion spectra for one or more of the known product ion spectra,
   d) calculating a score for the product ion traces and product ion spectra that represents how well the known product ions and sample product ions match, and
   e) calculating a quantitative value for the known compound from the product ion traces when the score exceeds a threshold value.

10. The method of claim 9, wherein each mass selection window of the plurality of mass selection windows has a width greater than 15 amu.

11. The method of claim 9, wherein the known compounds comprise one or more of peptides, proteins, complete proteomes, endogenous metabolites, lipids, carbohydrates, or combinations thereof.

12. The method of claim 9, wherein the known compounds comprise one or more compounds of pharmaceutical, environmental, forensic, or industrial importance.

13. The method of claim 9, wherein the known product ion spectra are determined from authentic standards of the known compounds, from an analysis of samples containing the compounds, from existing spectral libraries, or computationally generated by applying empirical or a priori fragmentation or modification rules to the known compounds.

14. The method of claim 9, further comprising using one or more matching sample product ions from step d) to identify a modified form of one or more compounds of the known compounds using the processor.

15. The method of claim 14, further comprising comparing the matching sample ions to masses predicted from known product ions and the modification to characterize a type and location of the modification using the processor.

16. The method of claim 14, further comprising extracting a spectrum of the identified modified form from the sample product ion spectra in order to characterize a type and location of the modification in the identified modified form using the processor.

17. A computer program product, comprising a tangible computer-readable storage medium whose contents include a program with instructions being executed on a processor so as to perform a method for quantitating detectable compounds of a sample, the method comprising:

provifing a system, wherein the system comprises one or more distinct software modules, and wherein the distinct software modules comprise a measurement module; and receiving sample product ion spectra for each mass selection window of a plurality of precursor mass selection windows for each time step of a plurality of time steps using the measurement module, wherein the sample product ion spectra are produced by separating detectable compounds in a sample over time, and at each time step analyzing the detectable compounds by performing a plurality of product ion scans for a plurality of precursor mass selection windows selected across a mass range of the sample using a tandem mass spectrometer; and searching the received product ion spectra for the presence of one or more known compounds with known product ion spectra using the measurement module by:
a) retrieving the known product ion spectra from a library,
b) retrieving the sample product ion spectra corresponding to the precursor mass selection window expected to contain a precursor ion corresponding to the known product ion spectra,
c) generating product ion traces in time for the sample product ion spectra for one or more of the known product ion spectra,
d) calculating a score for the product ion traces and product ion spectra that represents how well the known product ions and sample product ions match, and
e) calculating a quantitative value for the known compound from the product ion traces when the score exceeds a threshold value.

18. The computer program product of claim 17, further comprising using one or more matching sample product ions from step d) to identify a modified form of one or more compounds of the known compounds using the measurement module.

19. The computer program product of claim 18, further comprising comparing the matching sample ions to masses predicted from known product ions and the modification to characterize a type and location of the modification using the measurement module.

20. The computer program product of claim 18, further comprising extracting a spectrum of the identified modified form from the sample product ion spectra in order to characterize a type and location of the modification in the identified modified form using the measurement module.

* * * * *